(12) United States Patent
Conner et al.

(10) Patent No.: US 10,973,963 B2
(45) Date of Patent: Apr. 13, 2021

(54) NEGATIVE-PRESSURE THERAPY APPARATUS WITH PUSH-TO-RELEASE ACTUATOR

(71) Applicant: KCI Licensing, Inc., San Antonio, TX (US)

(72) Inventors: Ryan Conner, San Jose, CA (US); Crystal Musante, San Francisco, CA (US)

(73) Assignee: KCI Licensing, Inc., San Antonio, TX (US)

( * ) Notice: Subject to any disclaimer, the term of this patent is extended or adjusted under 35 U.S.C. 154(b) by 931 days.

(21) Appl. No.: 15/427,933

(22) Filed: Feb. 8, 2017

(65) Prior Publication Data

US 2017/0224885 A1    Aug. 10, 2017

Related U.S. Application Data

(60) Provisional application No. 62/293,318, filed on Feb. 9, 2016.

(51) Int. Cl.
*A61M 1/00* (2006.01)
*A61M 13/00* (2006.01)
*A61F 13/00* (2006.01)

(52) U.S. Cl.
CPC ..... *A61M 1/0023* (2013.01); *A61F 13/00068* (2013.01); *A61M 1/0003* (2013.01);
(Continued)

(58) Field of Classification Search
CPC ................................................ A61F 13/00068
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Partial ISR for corresponding PCT/US2017/018129, mailed May 15, 2017.

(Continued)

*Primary Examiner* — Guy K Townsend

(57) ABSTRACT

Example embodiments may include an apparatus for providing negative-pressure therapy with a push-to-release actuator. The actuator may be a key insertable through a keyway in the apparatus to engage a movable barrier, such as a piston. The actuator may also be used to lock the barrier in a primed position. Pressing on the actuator can release the barrier and activate the apparatus for negative-pressure therapy. In some examples, the actuator may comprise a shaft, a latch, and a spring biasing the latch toward the shaft. The latch may comprise an opening toward a proximal end of the shaft. The apparatus may comprise a receptacle for receiving the actuator, and a keeper may disposed within the receptacle for coupling to the latch. In some embodiments, the keeper may comprise a base protruding from the wall, and a ledge extending from the base toward the second aperture.

13 Claims, 15 Drawing Sheets

(52) U.S. Cl.
CPC .......... *A61M 1/007* (2014.02); *A61M 1/0009* (2013.01); *A61M 1/009* (2014.02); *A61M 1/0052* (2014.02); *A61M 1/0068* (2014.02); *A61M 1/0086* (2014.02); *A61M 1/0088* (2013.01); *A61M 2205/071* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Pokier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,174,306 B1 * | 1/2001 | Fleischmann ........ A61B 17/085 604/540 |
| 6,241,747 B1 | 6/2001 | Ruff |
| 6,287,316 B1 | 9/2001 | Agarwal et al. |
| 6,345,623 B1 | 2/2002 | Heaton et al. |
| 6,446,839 B1 * | 9/2002 | Ritsche ............... A61M 5/3158 222/153.13 |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| D618,337 S | 6/2010 | Pratt et al. |
| D624,177 S * | 9/2010 | Pratt .................... A61M 1/0072 D24/111 |
| 8,007,257 B2 * | 8/2011 | Heaton ............... A61M 1/0025 417/472 |
| 8,287,507 B2 * | 10/2012 | Heaton ............... A61M 1/0072 604/316 |
| 8,535,283 B2 * | 9/2013 | Heaton ............... A61M 1/0023 604/319 |
| 8,641,692 B2 * | 2/2014 | Tout .................... A61M 1/0011 604/316 |
| 8,679,079 B2 * | 3/2014 | Heaton ............... A61M 3/0262 604/313 |
| 8,728,045 B2 * | 5/2014 | Hu ....................... A61M 1/0072 604/319 |
| 8,728,046 B2 * | 5/2014 | Hu ....................... A61M 1/007 604/319 |
| 8,858,516 B2 * | 10/2014 | Hu ....................... A61M 1/0068 604/290 |
| 8,864,748 B2 * | 10/2014 | Coulthard ........... A61M 1/0068 604/543 |
| 10,548,778 B2 * | 2/2020 | Hassenpflug ....... A61M 1/0023 604/321 |
| 10,758,648 B2 * | 9/2020 | Conner ............... A61M 1/0049 604/321 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0020244 A1 * | 1/2006 | Schreijag ............. A61D 1/025 604/221 |
| 2007/0265586 A1 * | 11/2007 | Joshi .................. A61F 13/0216 604/313 |
| 2010/0042021 A1 * | 2/2010 | Hu ......................... F16L 37/36 601/6 |
| 2010/0228205 A1 * | 9/2010 | Hu ....................... A61M 1/0072 604/319 |
| 2011/0077605 A1 * | 3/2011 | Karpowicz ......... A61M 1/0029 604/318 |
| 2012/0071845 A1 * | 3/2012 | Hu ....................... A61M 1/007 604/319 |
| 2012/0083754 A1 * | 4/2012 | Hu ....................... A61M 1/007 604/319 |

(56) References Cited

U.S. PATENT DOCUMENTS

| | | | | |
|---|---|---|---|---|
| 2012/0209225 A1* | 8/2012 | Hu | | A61M 1/0096 604/319 |
| 2013/0144227 A1* | 6/2013 | Locke | | A61M 1/0035 604/318 |
| 2014/0100539 A1* | 4/2014 | Coulthard | | A61M 1/0088 604/319 |
| 2014/0200535 A1* | 7/2014 | Locke | | A61M 1/0088 604/321 |
| 2014/0276498 A1* | 9/2014 | Connor | | A61M 1/0088 604/321 |
| 2015/0018784 A1* | 1/2015 | Coulthard | | A61M 1/0031 604/319 |
| 2015/0094673 A1* | 4/2015 | Pratt | | A61M 1/0027 604/318 |
| 2015/0094674 A1* | 4/2015 | Pratt | | A61M 1/0035 604/318 |
| 2017/0224885 A1* | 8/2017 | Conner | | A61M 1/0088 604/321 |
| 2018/0169308 A1* | 6/2018 | Hu | | A61M 1/007 604/321 |
| 2019/0298576 A1* | 10/2019 | Hassenpflug | | A61M 1/0068 604/321 |
| 2019/0298899 A1* | 10/2019 | Hu | | A61M 1/0066 604/321 |
| 2020/0246514 A1* | 8/2020 | Conner | | A61M 1/0009 604/321 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2009154871 A1 | 12/2009 |
| WO | 2013078214 A1 | 5/2013 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., MD., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

(56) References Cited

OTHER PUBLICATIONS

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

International Search Report and Written opinion for corresponding Application No. PCT/US2017/017040, dated Jul. 4, 2017.

* cited by examiner

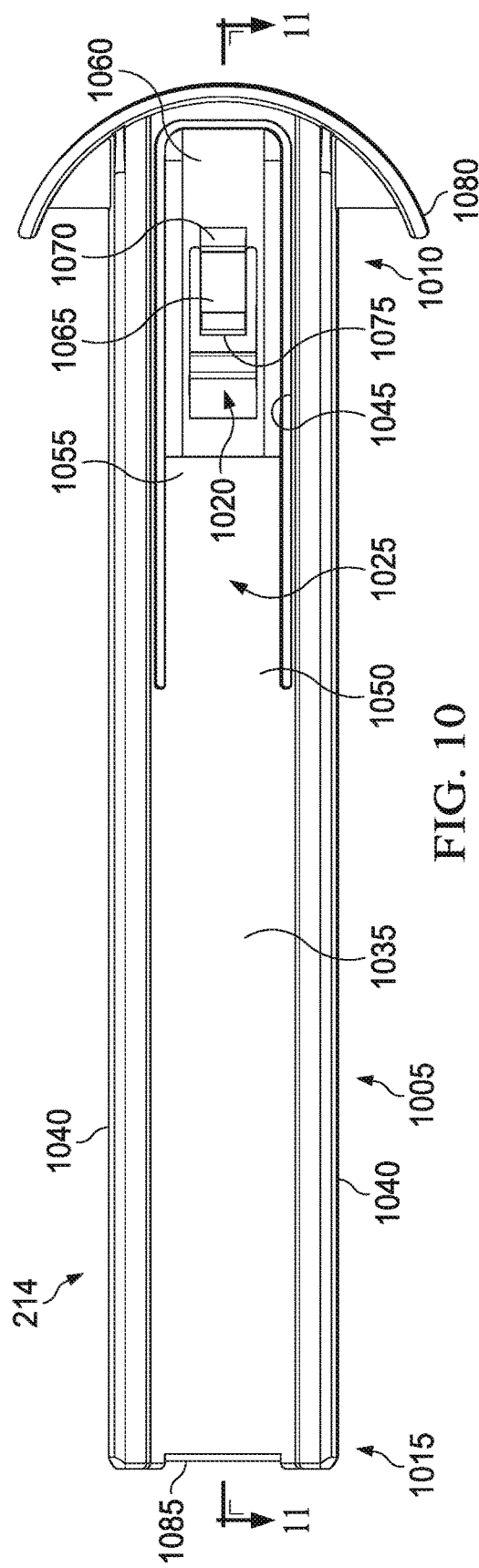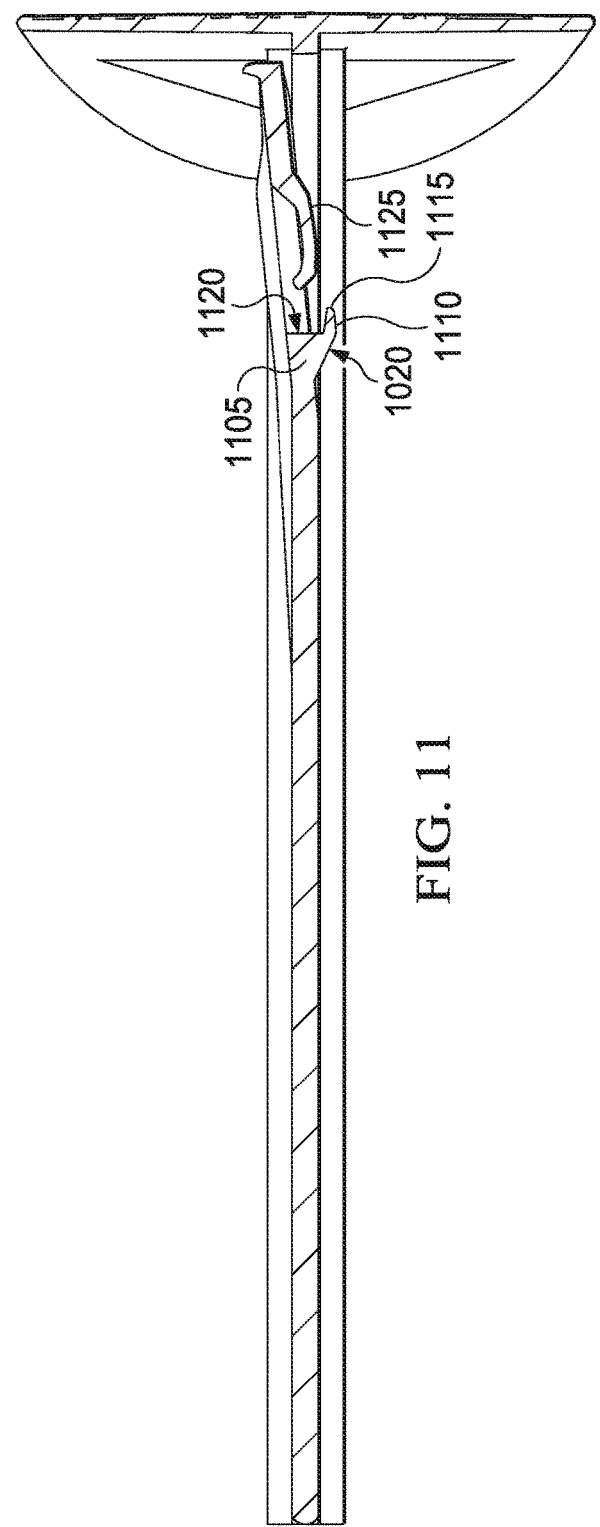

NEGATIVE-PRESSURE THERAPY APPARATUS WITH PUSH-TO-RELEASE ACTUATOR

RELATED APPLICATION

This application claims the benefit, under 35 USC § 119(e), of the filing of U.S. Provisional Patent Application Ser. No. 62/293,318, entitled "A NEGATIVE-PRESSURE THERAPY APPARATUS WITH PUSH-TO-RELEASE ACTUATOR" filed Feb. 9, 2016, which is incorporated herein by reference for all purposes.

TECHNICAL FIELD

The invention set forth in the appended claims relates generally to tissue treatment systems and more particularly, but without limitation, to negative-pressure therapy with a manually-actuated piston and a push-to-release actuator.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for providing negative-pressure therapy are set forth in the appended claims. Illustrative embodiments are also provided to enable a person skilled in the art to make and use the claimed subject matter.

For example, in some embodiments, an apparatus for providing negative-pressure therapy may comprise a housing and a barrier disposed in the housing. The barrier may be a reciprocating piston or flexible diaphragm in some embodiments. The barrier may divide the housing into two chambers, and movement of the barrier within the housing can vary the volume of each of the chambers accordingly. The barrier can also provide a fluid seal between the two chambers in some embodiments. A negative-pressure port may be fluidly coupled to one of the chambers, and movement of the barrier to expand the volume of the chamber can reduce the pressure of fluid in the chamber. Movement of the barrier may be effectuated manually in some embodiments. For example, one or more elastic elements may be operatively coupled to the barrier so that movement of the barrier to reduce the volume of the chamber fluidly coupled to the negative-pressure outlet also extends the elastic elements from a neutral state, thereby causing a restoring force to be applied to the barrier. A force contrary to the elastic force may be applied to the barrier by an actuator in some embodiments. For example, the actuator may be a key that can be inserted through an appropriate keyway in the housing to engage the barrier and move the barrier to prime (or charge) the apparatus for negative-pressure therapy. The actuator may also be used to lock the barrier in the primed position in some embodiments. Pressing on the actuator again can release the barrier to activate the apparatus for therapy.

In some embodiments, the housing may comprise an ellipsoidal cylinder, and the barrier may be a sliding seal concentrically disposed therein. The chambers have a variable effective volume defined by the distance between the position of the seal and an opposing end of the chamber. The seal may be connected to one or more elastic elements, such as a spring, which may be used to bias the seal towards increasing the volume of one of the chambers. The springs may have any of a variety of configurations, including ribbon springs. The ribbon spring may be a substantially constant-force spring or a variable-force spring. In some examples, a combination of spring types may be used. In still other examples, a single ribbon may be configured with a coil at each end and attached to a slidable seal at a middle region of the single ribbon. The force exerted on the seal may vary, but a spring force of less than 20 pounds may be suitable for some applications. In some embodiments, the spring force may be less than 0.5 pounds.

More generally, example embodiments of an apparatus for priming a therapy unit are described. The apparatus may be an actuator comprising a shaft, a latch, and a spring biasing the latch toward the shaft. The shaft may further comprise a proximal end and a distal end, and the distal end may be configured for insertion through an opening in a housing of the therapy unit to engage a movable barrier, such as a piston. The latch is generally configured for releasably coupling to a keeper disposed in the housing, and the latch may comprise an opening toward the proximal end of the shaft. In some embodiments, the shaft may be a beam, and the spring may be flat spring or a cantilever spring. For example, in some embodiments, the spring may be a flat spring or a cantilever spring disposed within a plane of the shaft. Additionally, a centralizer may be configured to bias the latch or the spring toward the shaft. The centralizer may comprise a bow in some embodiments. In more particular example embodiments, the shaft may comprise an aperture, and the spring may be a cantilever spring coupled to the shaft and disposed within the aperture.

Additionally or alternatively, example embodiments of an apparatus for releasably retaining a priming apparatus, such as an actuator. In some embodiments, the apparatus may comprise a receptacle, and the receptacle may comprising a wall defining a first aperture and a second aperture. The first aperture may be configured for receiving a distal end of the actuator and the second aperture may be disposed opposite the first aperture and aligned for passage of the distal end of the actuator. A keeper may disposed within the receptacle between the first aperture and the second aperture. In some embodiments, the keeper may comprise a base protruding from the wall, and a ledge extending from the base toward the second aperture.

Systems for providing negative-pressure therapy are also described herein, wherein some example embodiments include a housing having a keyway or other opening for receiving a priming key or other actuator. A piston or other barrier may be reciprocably disposed within the housing and dividing the housing into a proximal chamber and a distal chamber. A negative-pressure port may be fluidly coupled to the distal chamber. In some embodiments, an elastic element, such as a piston spring, may be coupled to the piston for expanding the distal chamber. A keeper may be disposed in the housing between the piston and the keyway. The system may additional comprise a key for moving the piston against the piston spring to a charged position. Some embodiments of the key may comprise a shaft, a latch, and another elastic element, such as a priming spring. The shaft may comprise an engagement end for passage through the keyway and pushing against the piston. The priming spring may couple the latch to the shaft for biasing the latch toward a release position. The system may additionally include a lever operable to move the latch to a lock position in opposition to the priming spring, so that the latch engages the keeper if the piston is released from the charged position while the latch is in the lock position and the latch disengages the keeper if the piston is released from the charged position while the latch is in the release position.

The system may additional include a bump disposed in the housing between the keeper and the keyway in some embodiments. A centralizer pocket may also be disposed in the housing between the bump and the keyway, and a centralizer may be coupled to the lever. The centralizer may be configured to rest in the centralizer pocket if the latch is in the lock position, and may be further configured to engage the bump if the piston is released from the charged position while the latch is in the release position.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 10 is a front view of the actuator of FIG. 4;

FIG. 11 is a section view of the actuator of FIG. 10;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
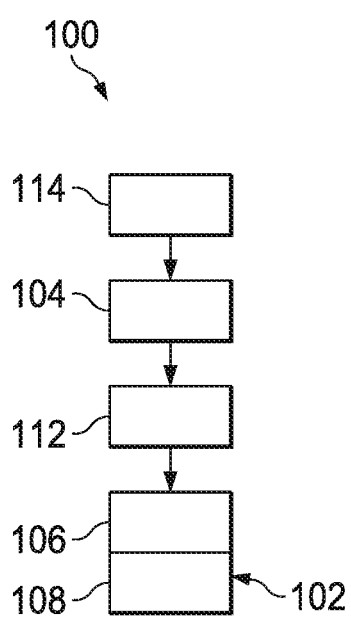
FIG. 1 is a functional block diagram of an example embodiment of a therapy system that can provide negative-pressure therapy in accordance with this specification.

FIG. 1 is a simplified functional block diagram of an example embodiment of a therapy system 100 that can provide negative-pressure therapy in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a tissue interface 108.

In some embodiments, a dressing interface may facilitate coupling the negative-pressure source 104 to the dressing 102. For example, such a dressing interface may be a T.R.A.C.® Pad or Sensa T.R.A.C.® Pad available from KCI of San Antonio, Tex. The therapy system 100 may optionally include a fluid container, such as a container 112, coupled to the dressing 102 and to the negative-pressure source 104.

Additionally, the therapy system 100 may include sensors to measure operating parameters and provide feedback signals indicative of the operating parameters. For example, the therapy system 100 may include a pressure sensor, an electric sensor, or both, coupled to a controller. The pressure sensor may also be coupled or configured to be coupled to a distribution component and to the negative-pressure source 104.

Components may be fluidly coupled to each other to provide a path for transferring fluids (i.e., liquid and/or gas) between the components. For example, components such as the dressing 102 and the negative-pressure source 104 may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be an apparatus that can reduce the pressure in a sealed volume, such as a vacuum pump or a suction pump, having an actuator 114. A negative-pressure supply may be housed within or used in conjunction with other components, such as sensors and alarm indicators, for example. In some embodiments, the negative-pressure source 104 may be combined with other components into a therapy unit. For example, in some embodiments, the container 112, the actuator 114, or both may be integral with the negative-pressure source 104. A negative-pressure supply may also have one or more supply ports configured to facilitate coupling and de-coupling the negative-pressure supply to one or more distribution components.

In some embodiments, the actuator 114 may be manually operated to prime the negative-pressure source. In some embodiments, for example, the negative-pressure source 104 may be primed or charged before providing negative-pressure. Priming or charging the negative-pressure source 104 generally refers to any act or actions for preparing or putting the negative-pressure source 104 in a state or condition to generate negative pressure. The negative-pressure source 104 may also be activated after being primed or charged. In some configurations, the charging and activating may be performed in a single continuous step, while in other configurations, the charging and the activating method may be performed in distinctly separate steps.

For example, some embodiments of the negative-pressure source 104 may comprise a moving seal disposed in a working chamber. In some embodiments, for example the seal may be a piston or other barrier configured to reciprocate between a proximal end and a distal end of a working chamber, and the negative-pressure source 104 may be primed by positioning the piston at a distal end. The seal may be positioned by any of a variety of priming mechanisms or actuators, such the actuator 114. The actuator 114 may be a priming key, slider, or push rod, for example. In some embodiments, a force mechanism may be applied to the actuator 114 to move the seal, and the seal may automatically begin to slide back to generate a negative pressure if the force is released. In other embodiments, the negative-pressure source 104 may comprise an activating or release mechanism that is actuated separately from a priming mechanism to initiate the generation of the negative pressure. In some configurations, the activating mechanism may directly block or restrict movement of the sliding seal, while in other configurations, the activating mechanism may restrict or limit flow of fluid into or out of the working chamber. In some examples, the release mechanism may comprise a separate button or lever that is configured to alter communication or flow through a valve coupled to the working chamber.

In some embodiments, the actuator 114 may comprise or consist of a priming key or tool configured to displace sliding seal into a primed position. In some examples, the priming key may comprise an elongate rigid member configured to be positioned in an opening or keyway of the negative-pressure source 104. In some embodiments, the priming key can be used to mechanically move a sliding seal towards a distal end of working chamber until a latch, embedded within the shaft of the priming key, locks into place. In some embodiments the actuator 114 may also serve as a cap to close a working chamber. In some embodiments, the actuator 114 may be configured to hold and maintain the negative-pressure source 104 in a charged state. In other embodiments, the actuator 114 can also be configured for recharging the negative-pressure source 104. For example, the actuator 114 may be used to recharge the negative-pressure source 104 if a leak cause substantial discharge or after emptying the container 112.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy. In some embodiments, the container 112 may be integral with other components, such as the dressing 102 or the negative-pressure source 104.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

Figure 2:
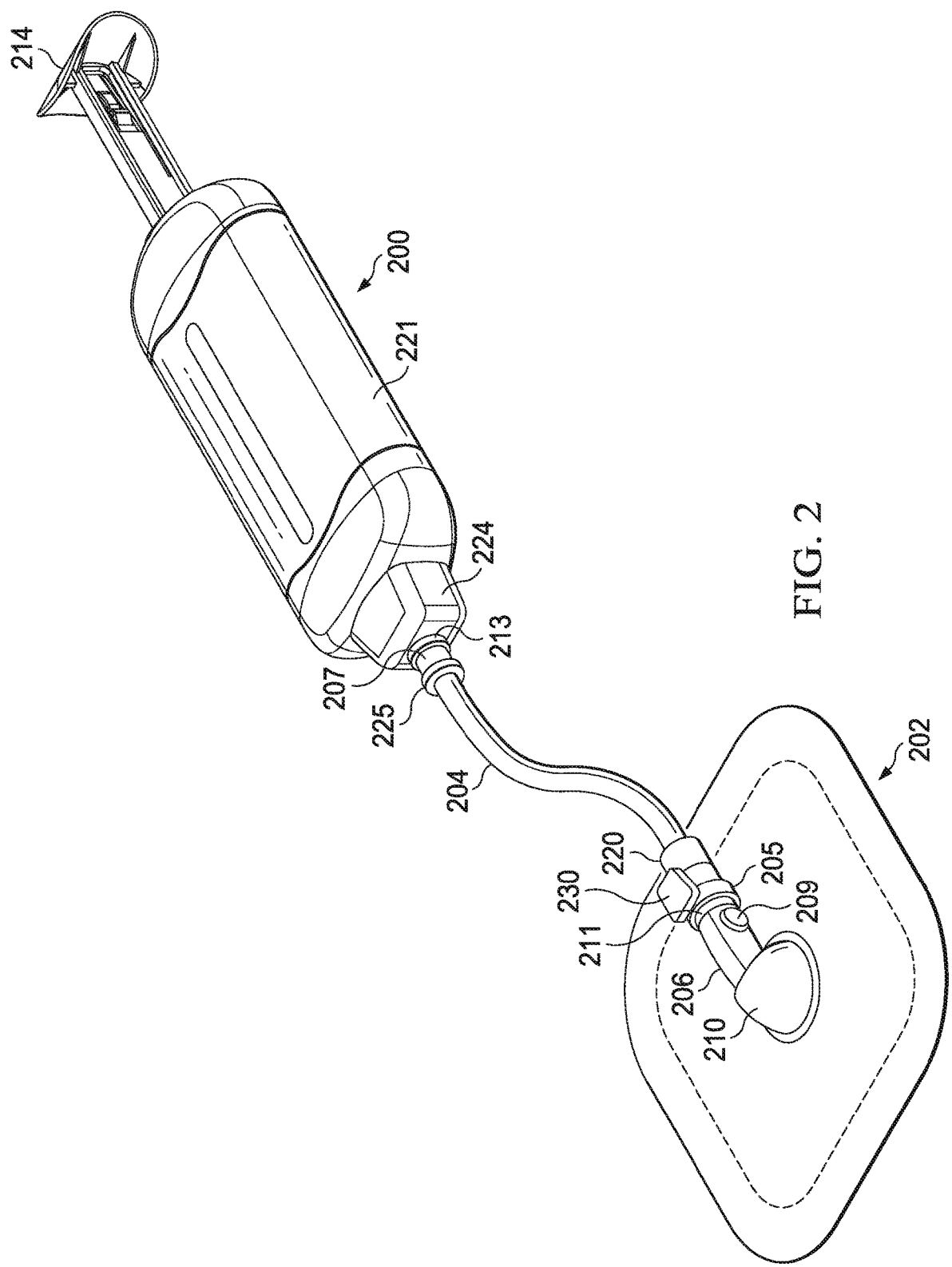
FIG. 2 is a schematic diagram illustrating additional details that may be associated with some example embodiments of therapy system of FIG. 1.

FIG. 2 is a schematic diagram illustrating additional details that may be associated with some example embodiments of the therapy system 100. In the example embodiment of FIG. 2, the therapy system 100 generally includes a therapy unit 200, a dressing 202, and a tube 204. The therapy unit 200 is an example of an apparatus in which the negative-pressure source 104 may be combined with other components. For example, in some embodiments, the therapy unit 200 may include the negative-pressure source 104 and the container 112 (not shown in FIG. 2) integrally combined within a housing of the therapy unit 200. As illustrated in the example embodiment of FIG. 2, the therapy system may also include an actuator 214, which may be an example of the actuator 114 of FIG. 1.

The dressing 202 may be an example embodiment of the dressing 102. An integrated attachment port 206 may be configured to connect the dressing 202 to the tube 204, or directly to the therapy unit 200. In some embodiments, the tube 204 or the therapy unit 200 may be configured to rotate about an axis of the attachment port 206. In some embodiments, the attachment port 206 may be configured to rotate around a base 210 and/or to bend toward and/or away from the dressing 202. For example, the attachment port 206 may be configured to freely rotate about 360 degrees or more, or to provide a limited rotation range less than about 360 degrees. The attachment port 206 may have a fixed orientation that is generally parallel to the plane of the sealant layer, but in other configurations, may be angled below the parallel plane or above the parallel plane. In still other examples, the attachment port 206 may be configured to bend or pivot relative to the dressing 202. The range of bending or pivoting may be from about 0 degrees to about 45 degrees or about 90 degrees, from about 0 degrees to 135 degrees or about 180 degrees, or from about −15 degrees or about −30 degrees to about 45 degrees, about 90 degrees, about 135 degrees, about 180 degrees, 195 degrees or about 210 degrees. In certain embodiments, the attachment port 206 may be configured to rotate and pivot.

The therapy unit 200 or the tube 204 may be coupled to the attachment port 206 by any of a variety of mechanisms. For example, the attachment port 206 may comprise a resistance or interference fitting which may be inserted into the tube 204 or a connector interface 211 of the therapy unit 200. The resistance fitting may comprise one or more flanges configured to resist decoupling. In other examples, the tube 204 may be inserted into the lumen or opening of the attachment port, and the attachment port may comprise a push-in fitting, such as a John Guest fitting (Middlesex, UK). In other embodiments, connectors on both components may be used, including threaded or mechanical interlocking fits. The connectors may be configured to facilitate both coupling and decoupling of the components.

In the example embodiment depicted in FIG. 2, one end of the tube 204 comprises a port connector 205 configured to couple to a connector interface 211 of the attachment port 206, and the other end may comprise a therapy unit connector 207 configured to couple to the connector interface 213 of the therapy unit 200. In the example embodiment of FIG. 2, the connector interface 211 of the attachment port 206 and the therapy unit connector 207 of the tube 204 may comprise male-type connectors, while the connector interface 213 of the and the port connector 205 of the tube 204 may comprise female-type connectors. The particular male-female configuration described above is merely exemplary, and in other embodiments, the male/female configuration may be reversed, any other type of complementary interface may be used, including interfaces which are non-directional and permit the connector of the tube 204 in any direction. These or other complementary configurations may be used to permit both the direct connection of the therapy unit 200 and the dressing 202, as well as the optional use of the tube 204. In some embodiments, more than one of the tube 204 may be joined together. The tube 204 may also comprise one or more stress-relief or anti-kink structures, such as a helical winding or other tubular support, which may resist pinching or other deformations of the tube. In FIG. 2, for example, the port connector 205 and the therapy unit connector 215 of the tube 204 may comprise flared openings 220 and 225, respectively, which can permit at least some deflection of the tube 204 relative to the port connector 205 and the therapy unit connector 215 while distributing the bending stress along the length of the flared openings 220 and 225 to resist pinching. In other embodiments, the stress relief structures of the connectors may comprise one or more bendable or deformable projections, which may or may not be flared.

One or more connectors may also comprise a locking mechanism to facilitate decoupling and/or attachment. In some examples, a locking mechanism may resist inadvertent decoupling from the therapy unit 200 and/or the dressing 202. In the example depicted in FIG. 2, the port connector 205 comprises a locking mechanism with a connector-release button 230 configured to resist decoupling until the button 230 is pressed. The connector-release button 230 may be coupled to a movable structure that forms an interlocking or resistance fit with a complementary structure or surface on the attachment port 206. In some embodiments, the connector-release button 230 may be spring loaded or otherwise biased, and may or may not provide additional sealing and/or locking force between the port connector 205 and the attachment port 206. In other variations, other locking interfaces, including sliders, levers or knobs, may be used. The attachment port 206 may comprise one or more gripping materials or textured gripping surfaces 209. The gripping surface 209 on the exterior of the attachment port 206 may facilitate manual connection and disconnection of the connectors on the tube 204 or the therapy unit 200. The grip surface 209 may comprise one or more flanges or ridges, for example, and/or a high traction material such as rubber or a block copolymer with polystyrene and polybutadiene regions, e.g., KRATON® polymers by Kraton Polymers, LLC (Houston, Ill.). Gripping materials or structures may also be provided on the connectors 205 and 215 and/or the therapy unit 200. In FIG. 2, for example, the therapy unit 200 may comprise a nosepiece 224 having a reduced width relative to a body 221 of the therapy unit 200.

The nosepiece 224 may facilitate gripping of the therapy unit 200 when detaching the tube 204 or the attachment port 206, for example.

In some embodiments, the therapy unit 200 may comprise a rigid polymer configured to generally maintain its shape under negative pressure. The therapy unit 200 can be made of any suitable polymer such as polycarbonate, co-polyester, polyethylene, polypropylene, acrylic, ABS, glass, or any other polymer known to those skilled in the art.

Figure 3A:
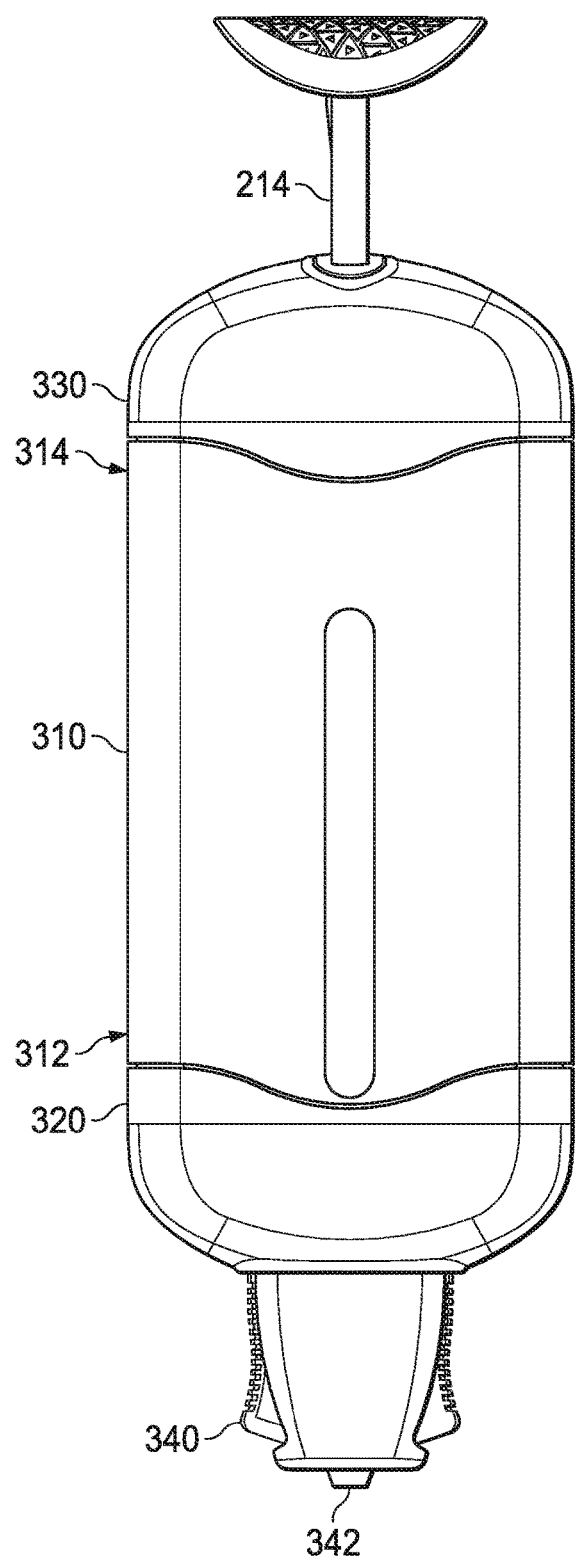
FIG. 3A and FIG. 3B are front views of the therapy unit of FIG. 2.
Figure 3B:
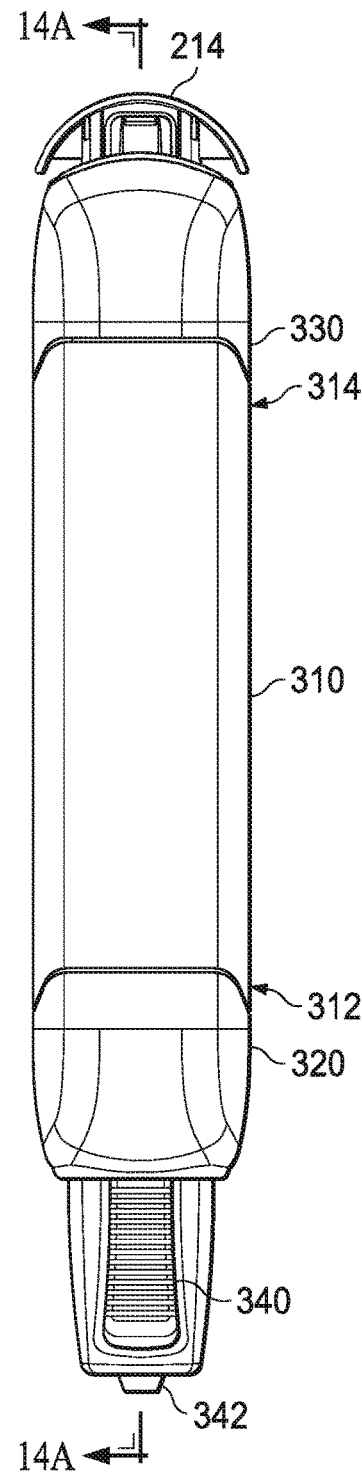

FIG. 3A and FIG. 3B are front views of the therapy unit 200 of FIG. 2, illustrating additional details that may be associated with some embodiments. FIG. 3A is illustrative of the therapy unit 200 with the actuator 214 in an unlocked position, and FIG. 3B is illustrative of the therapy unit 200 with the actuator 214 in a locked position. In the example of FIG. 3A and FIG. 3B, the therapy unit 200 comprises a housing 310 having a distal end 312, a proximal end 314, a distal cap 320, and a proximal cap 330. The distal cap 320 and the proximal cap 330 may be configured to be detachably secured to the distal end 312 and the proximal end 314 of the housing 310, respectively. A fitting housing 340 may be coupled to the distal cap 320, enclosing a fitting 342 that may be configured to connect the therapy unit 200 with another component of the therapy system 100.

The housing 310 may be fabricated from a rigid polymer adapted to maintain the external shape of the suction chamber shape under reduced pressure. In some embodiments, the entire body of the housing 310 may be transparent. In other embodiments, the housing 310 may comprise a non-transparent body but with an inspection window. In some example embodiments, the housing 310 may have a longitudinal axis and an elliptical cross-section transverse to the longitudinal axis.

Figure 4:
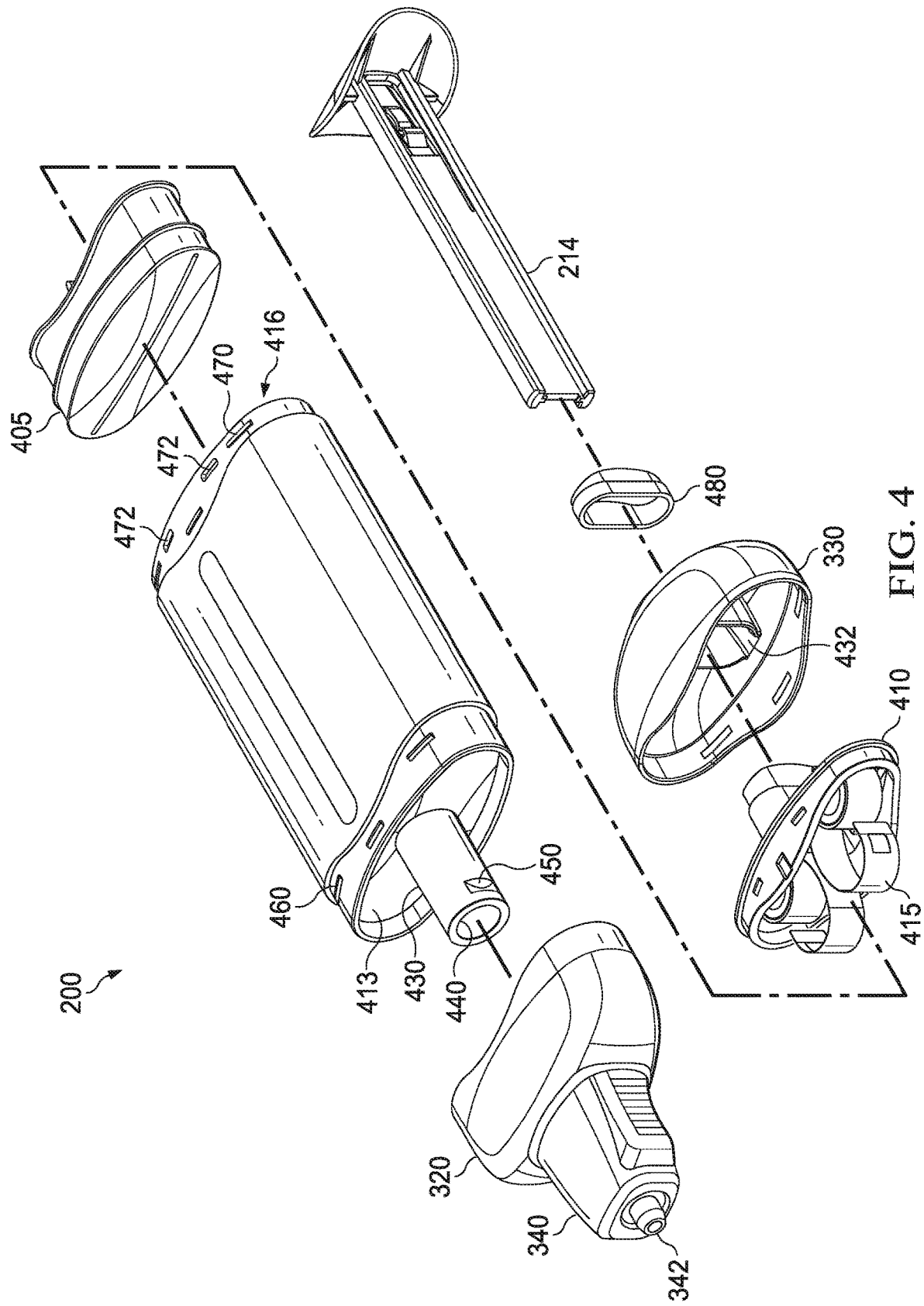
FIG. 4 is an exploded view of the therapy unit of FIG. 2.

FIG. 4 is an exploded view of the therapy unit 200, illustrating additional details that may be associated with some embodiments. The fitting housing 340 may be configured to removably detach from to the distal cap 320 in some example embodiments, while in other examples, the fitting housing 340 may be integrally formed with the distal cap 320 or otherwise configured not to be detached once joined. The therapy unit 200 may additionally include a piston or other barrier, such as a piston assembly 405, and one or more elastic elements, such as springs 415. The therapy unit 200 may also have a spring assembly 410 in some embodiments.

An opening such as a keyway 432 may be provided in the proximal cap 330 to permit insertion of the actuator 214. The distal end 312 and/or the proximal end 314 of the housing 310 may also comprise notches 460 and 470, respectively, which may be configured to facilitate coupling to the distal cap 320 and/or the proximal cap 330, respectively. Notches 472 or apertures may also be provided for attaching the spring assembly 410 to the housing 310.

FIG. 4 further illustrates a distal end wall 413 and a proximal opening 416 of the housing 310, and a removable seal 480. The distal end wall 413 may further comprise a conduit 430 or other extension structure in some embodiments. The conduit 430 may comprise a conduit lumen 440. The conduit 430 may comprise any of a variety of grooves, flanges, or notches 450, which may facilitate attachment of the conduit 430 to one or more components associated with the fitting housing 340.

Figure 5:
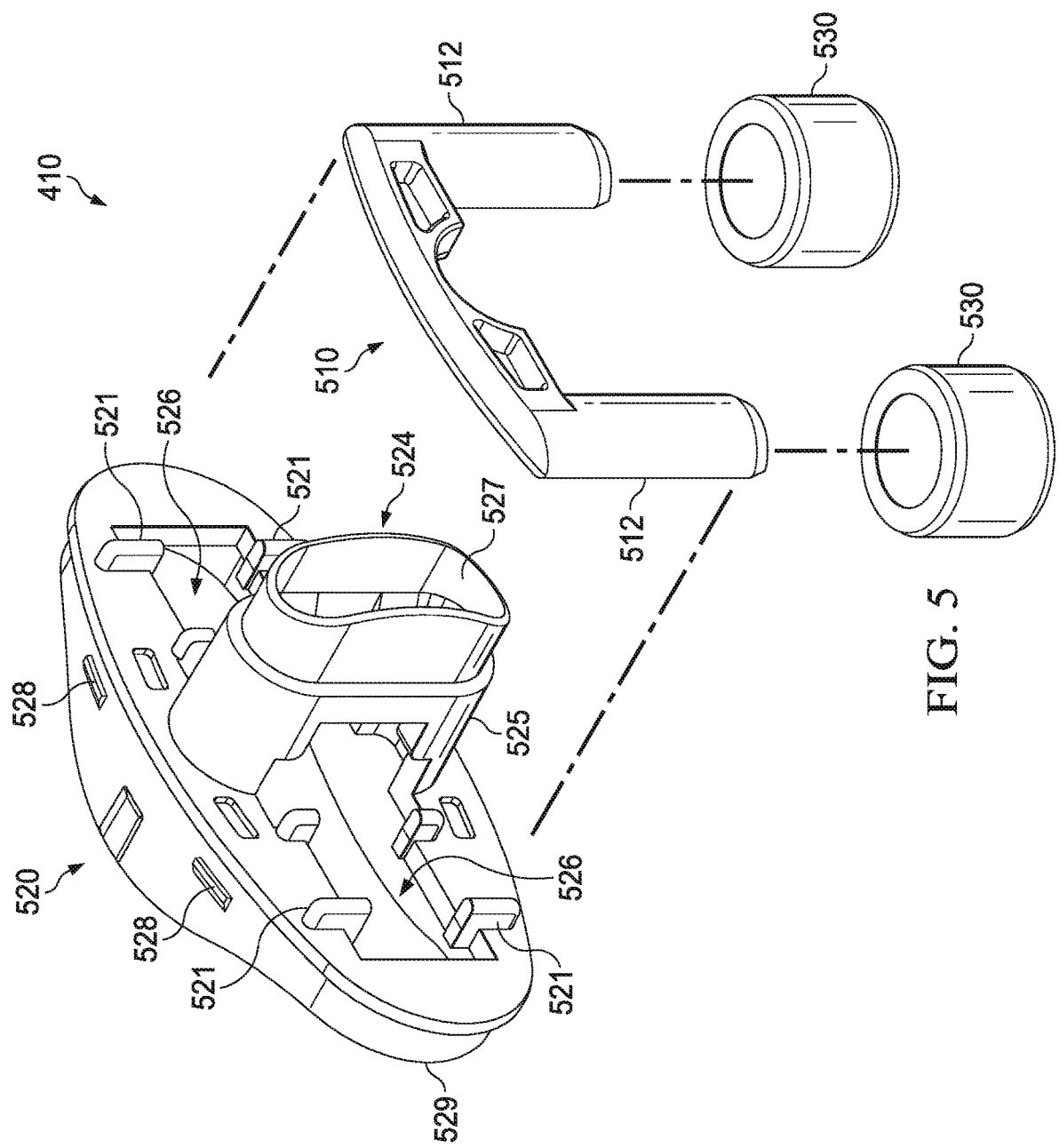
FIG. 5 and FIG. 6 are component views of the spring assembly of FIG. 4.
Figure 6:
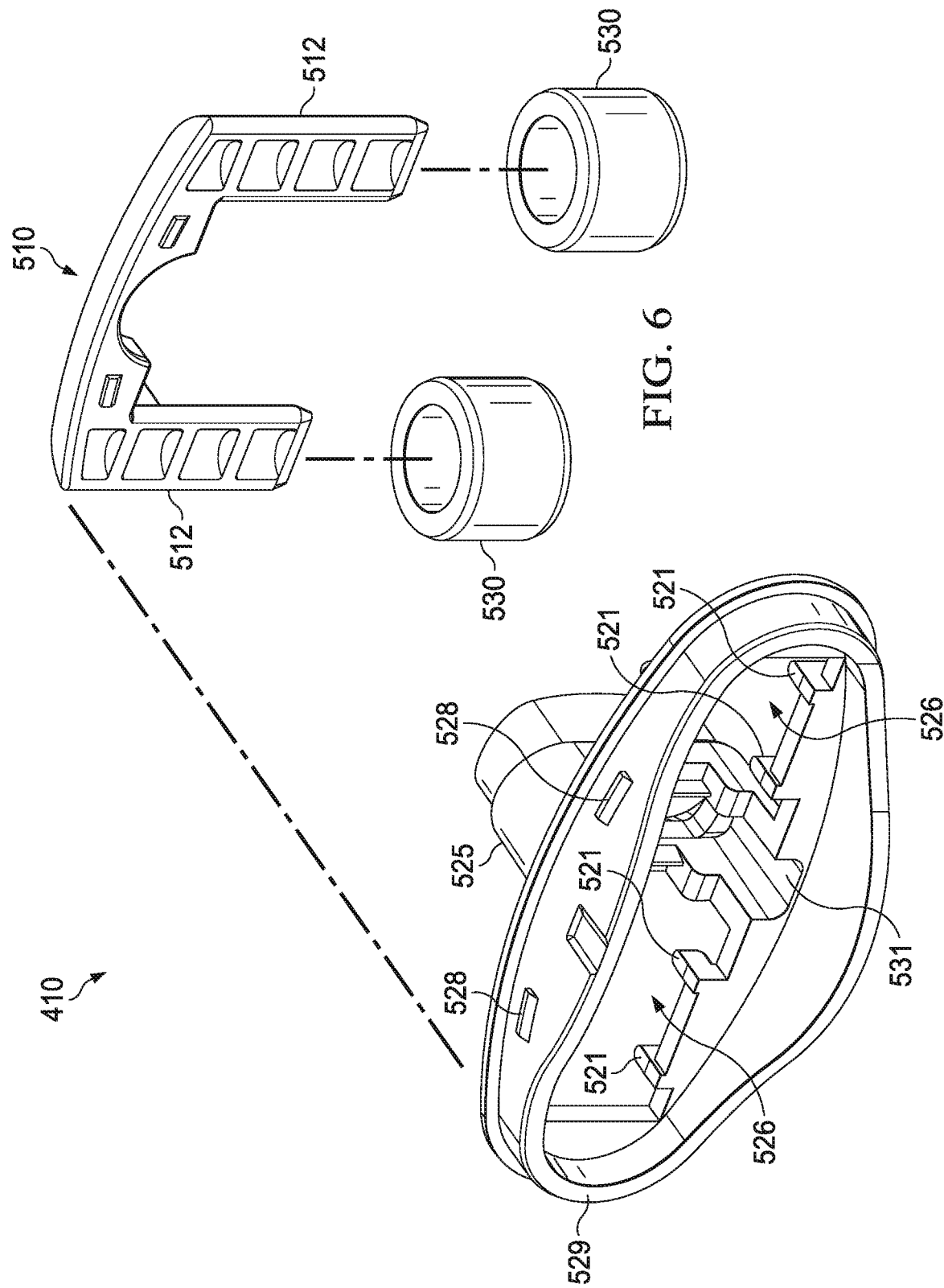

FIG. 5 and FIG. 6 are component views of the spring assembly 410, illustrating additional details that may be associated with some example embodiments. In some embodiments, the spring assembly 410 can be mounted at the proximal end 314 of the housing 310 and covered by the proximal cap 330. As illustrated in the example of FIG. 5, the spring assembly 410 may comprise a spring carrier 520, a U-shaped spring retainer 510, and two bushings 530 mounted on rails 512 of the spring retainer 510. The spring carrier 520 may comprise a receptacle 524 and two openings 526. The receptacle 524 may comprise a wall 525 defining a first aperture 527 and a second aperture 531. The receptacle 524 is configured to permit passage of the actuator 214 through the spring assembly 410. For example, the first aperture 527 may be opposite the second aperture 531 and aligned for passage of one end of the actuator 214 through the receptacle 524. The openings 526 are configured to house the bushings 530 if the spring retainer 510 is coupled to the spring carrier 520. As shown in FIG. 5, multiple ridges 521 may be located adjacent the openings 526 to limit the movement of the bushings 530. Fixation structures 528 may be provided to form a snapfit or other type of interfit with complementary structures on the housing 310.

Figure 7:
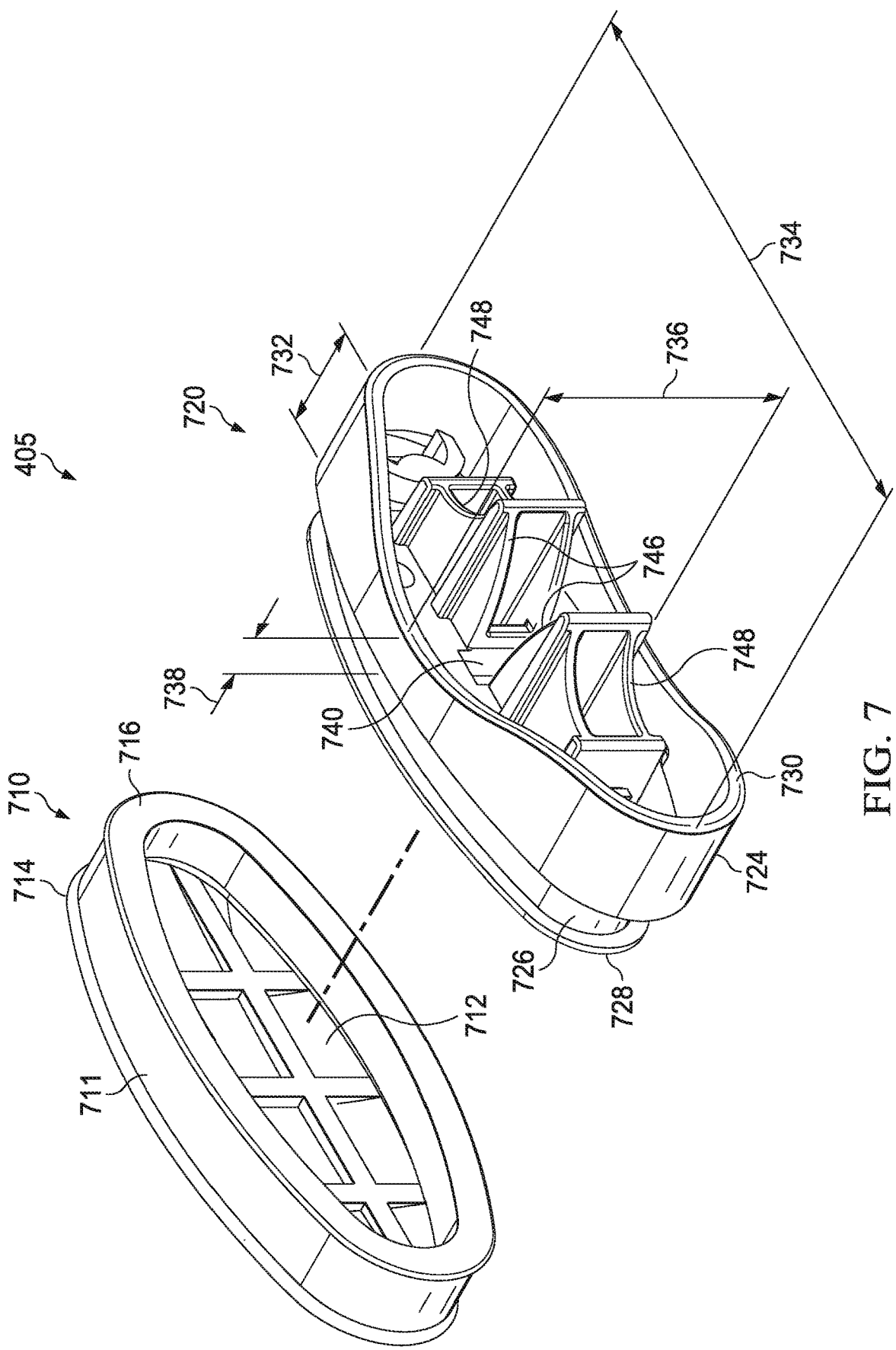
FIG. 7 and FIG. 8 are component views of the piston assembly of FIG. 4.
Figure 8:
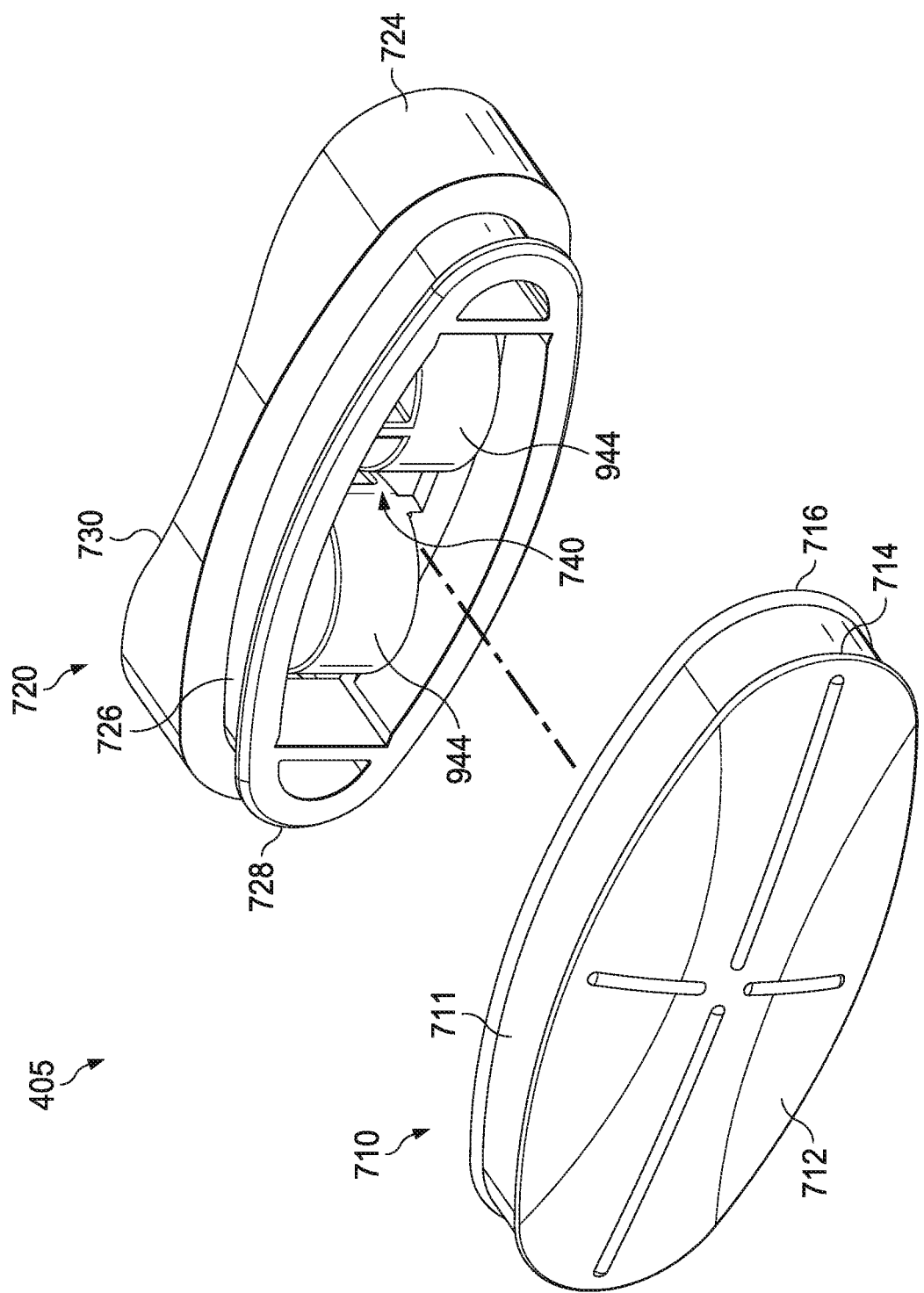

FIG. 7 and FIG. 8 are component views of the piston assembly 405, illustrating additional details that may be associated with some example embodiments. In the example embodiment of FIG. 7, the piston assembly 405 comprises a piston seal 710 and a piston 720. In the depicted embodiment, the piston seal 710 is elliptical, but other shapes may be suitable as well. The piston seal 710 may comprise a side wall 711 and a distal end wall 712. The side wall 711 of the piston seal 710 may further comprise a distal perimeter ridge 714 and a proximal perimeter ridge 716, the dimensions of which may be larger than that of the side wall 711 of piston seal 710. Exterior surfaces of the piston seal 710 may comprise a friction-reducing lubricant or a lubricious coating material.

The piston seal 710 may be detachably coupled to the piston 720 or in some embodiments, the piston seal 710 and the piston 720 may be integrally formed. In the example embodiment of FIG. 7, the piston 720 may comprise an elliptical frame with a side wall 724. The distal portion of side wall 724 may comprise a recess 726 and a raised edge or flange 728 configured form a complementary fit with the piston seal 710. The proximal perimeter edge 730 of the side wall 724 may be complimentary to the distal edge 529 of the spring assembly 410. In the example embodiment of FIG. 7, the proximal edge 730 has a curved, non-planar configuration. The piston seal 710 and/or the piston 720 may have a variable longitudinal length along its perimeter. In some instances, an increased longitudinal dimension may provide additional stability to the piston assembly 405. In some examples, the side length along a section of the perimeter of the piston 720 may be related to the transverse dimension intersecting a) that side length of the perimeter and b) the central movement axis of the seal and/or piston. In the example of FIG. 7, the lateral longitudinal surface of the piston 720 may have a longitudinal length 732 based upon the increased width 734 of the piston 720 relative to a height of the housing 310. In comparison, the superior longitudinal surface of the piston 720 may have a longitudinal length 738 that is smaller than the longitudinal length 732 of the lateral longitudinal surface from the reduced height 736 of the piston 720.

The piston 720 may also comprise a central opening 740. The central opening 740 may be configured to provide passage of springs, for example. The piston 720 may further comprise convex supports 746 adjacent to the central opening 740. In some example embodiments, the convex supports 746 may have a concave region 748.

Figure 9:
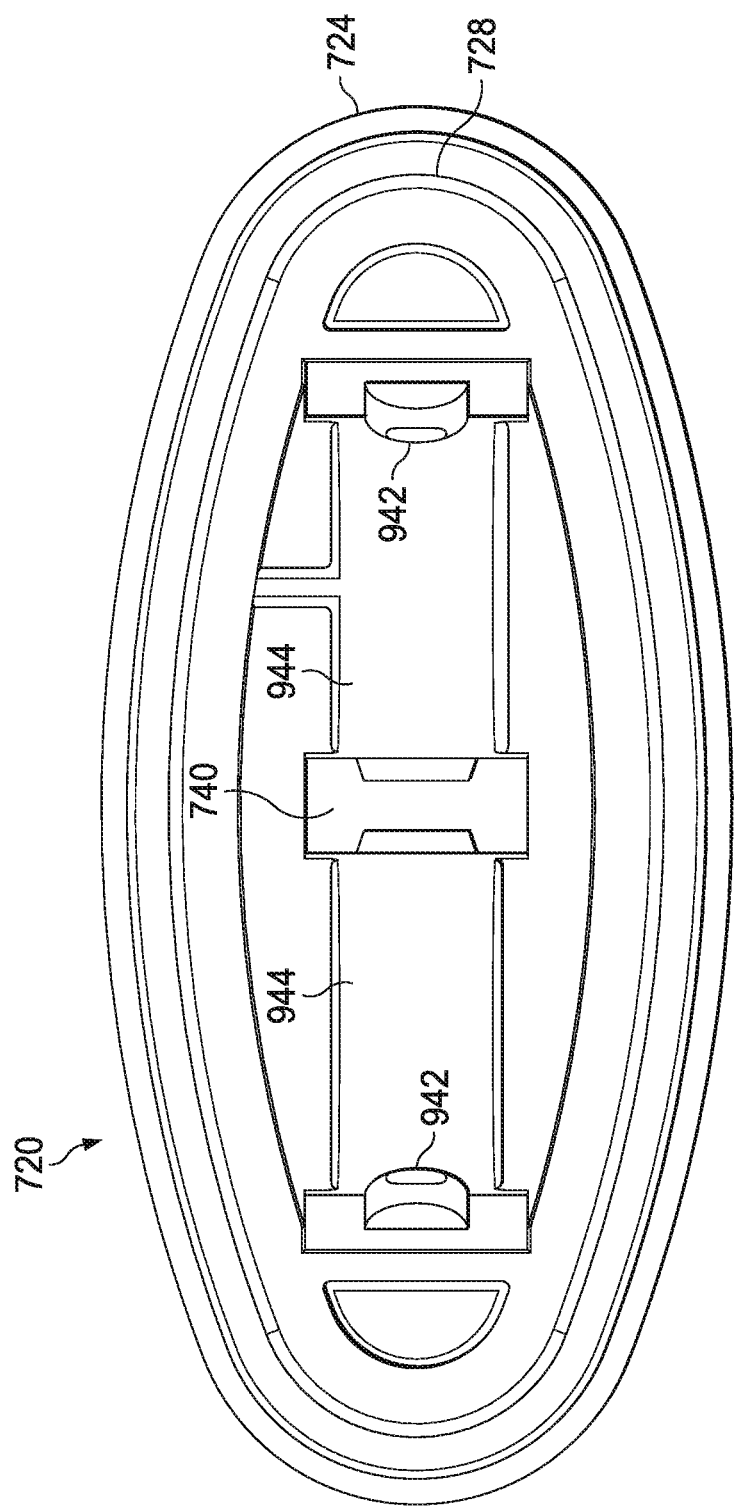
FIG. 9 is a front elevation view of the piston of FIG. 7 and FIG. 8.

FIG. 9 is a front elevation view of the piston 720, illustrating additional details that may be associated with some embodiments. For example, the piston 720 may include spring retaining structures 942 and curved support surfaces 944 extending between each of the retaining structures 942 and the central opening 740.

FIG. 10 is a front view of the actuator 214, illustrating additional details that may be associated with some example embodiments. As illustrated in FIG. 10, the actuator 214 may comprise a shaft 1005 having a proximal end 1010 and a distal end 1015. A latch 1020 may be coupled to the shaft 1005. For example, a spring 1025 may couple the latch 1020 to the shaft 1005.

As illustrated in the example of FIG. 10, the shaft 1005 may have a length substantially greater than its width or thickness. In some embodiments, the shaft 1005 may be a beam. For example, the shaft 1005 may be an I-beam having a web 1035 and flanges 1040. The flanges 1040 may increase bending moment resistance, and may also function as guide rails.

The spring 1025 is illustrative of any elastic object that can suitably store mechanical energy if disturbed from its neutral position, including a coil spring or a flat spring. The spring 1025 may be a flat spring in some embodiments, and may be parallel or coplanar to the shaft 1005 in some embodiments. In more particular examples, the spring 1025 may be a flat spring, which may have a neutral axis collinear with a neutral axis of the shaft 1005. For example, in the embodiment of FIG. 10, the shaft 1005 is a beam and the spring 1025 is a flat spring disposed with in an aperture 1045 of the shaft 1005, so that the spring 1025 and the shaft 1005 have collinear neutral axes and the spring 1025 lies within a plane defined by edges of the shaft 1005. In more particular example embodiments, the spring 1025 may be a cantilever spring having a first end 1050 and a second end 1055, wherein the first end 1050 is coupled to the shaft 1005 and the second end 1055 is free. In the example of FIG. 10, the second end 1055 is opposite the distal end 1015, and the first end 1050 is opposite the proximal end 1010.

In some example embodiments, the actuator 214 may further include a lever 1060 configured to operate the latch 1020. The lever 1060 may be coupled to the spring 1025 in some embodiments, or more specifically, may be integral with the spring 1025 as illustrated in the example of FIG. 10. If the lever 1060 is integral with the spring 1025 as shown in FIG. 10, the lever 1060 may be a flat lever and may also be disposed within the aperture 1045 so that the lever 1060 lies in the plane of the shaft 1005 and shares a neutral axis with the shaft 1005 and/or the spring 1025.

The actuator 114 may also comprise a centralizer 1065 in some example embodiments. The centralizer 1065 may be a rigid element, an elastic element, or a combination of rigid and elastic elements. As illustrated in the example of FIG. 10, the centralizer 1065 may be a cantilevered beam or spring, having a fixed end 1070 and a free end 1075 in some embodiments. The fixed end 1070 may be coupled to the spring 1025 or to the lever 1060 in some embodiments, and may be oriented so that free end 1075 is proximate to the latch 1020.

As shown in the example embodiment of FIG. 10, the actuator 214 may also comprise a handle 1080 and a distal end 1085. The handle 1080 may be coupled to the proximal end 1010 of the shaft 1005 in some embodiments. The handle 1080 preferably has a low profile and an ergonomic shape, and may be a saddle handle as illustrated in the FIG. 10. The distal end 1085 may be configured to be inserted through the keyway 432 and the receptacle 524 to engage the piston 720.

FIG. 11 is a section view of the actuator 114 of FIG. 10 taken along line 11-11. In some example embodiments, the latch 1020 may comprise or consist of a hook having a point and a throat open toward the proximal end 1010. For example, as illustrated in the embodiment of FIG. 11, the latch 1020 may be a hook latch comprising a base 1105 and a bar 1110 forming a point 1115 and a throat 1120. In some embodiments, the base 1105 may be a spacer coupled to the spring 1025, and the bar 1110 may be coupled to the base 1105, as illustrated in FIG. 11. In some embodiments, the bar 1110 may be obliquely coupled to the spring to form the point 1115 and the throat 1120.

FIG. 11 also illustrates additional details that may be associated with some embodiments of the centralizer 1065. For example, the centralizer 1065 may be or may comprise a spring having a bow 1125, as illustrated in FIG. 11. The bow 1125 is representative of a bow, arc, curve, bend, bump, protrusion, or other structure that provides an intermediate surface that is offset from at least one of its ends. The bow 1125 of FIG. 11, for example, provides an intermediate surface that is offset from the fixed end 1070.

Figure 12:
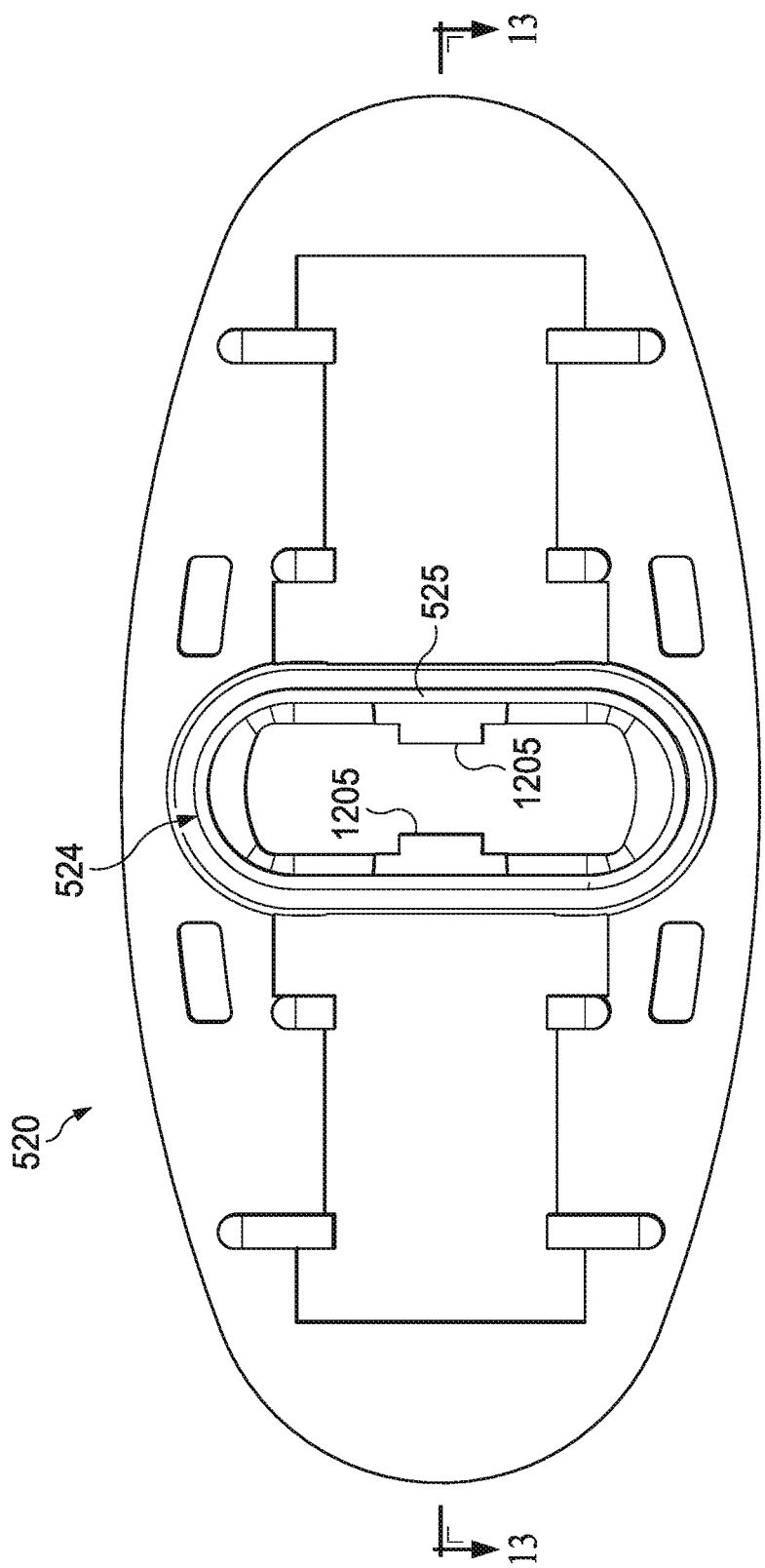
FIG. 12 is a front view of the spring carrier of FIG. 5 and FIG. 6.

FIG. 12 is a front view of the spring carrier 520, illustrating additional details that may be associated with some example embodiments. For example, at least one keeper 1205 may be disposed within an interior of the receptacle 524. In the example embodiment of FIG. 12, the receptacle 524 is generally symmetrical and comprises a keeper 1205 on opposing sides of the wall 525. The receptacle 524 may additional include guide channels 1210 in some embodiments, which are preferably configured to slidingly receive the flanges 1040 of the actuator 214.

Figure 13:
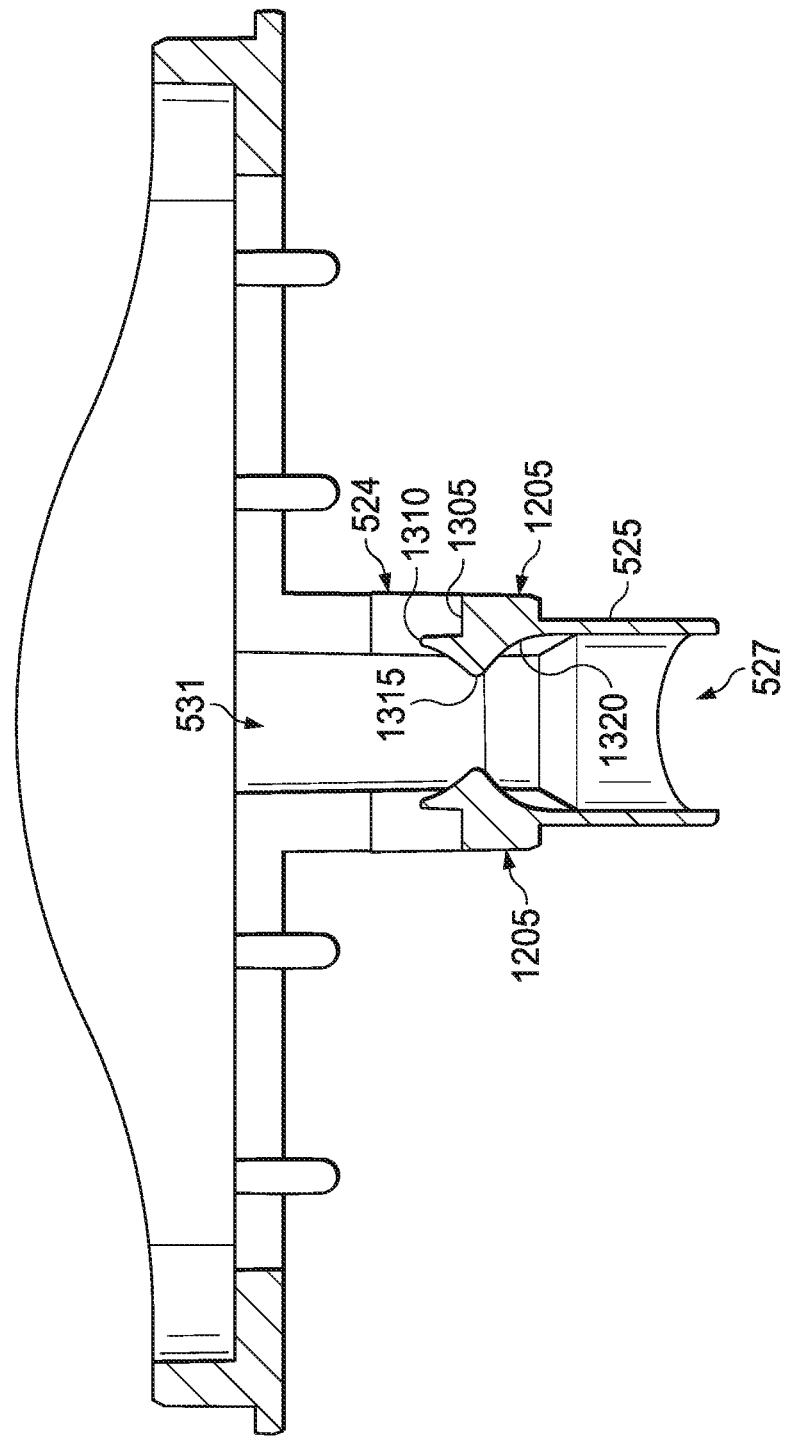
FIG. 13 is a section view of the spring carrier of FIG. 12.

FIG. 13 is a section view of the spring carrier 520 of FIG. 12 taken along line 13-13. As illustrated in FIG. 13, the keeper 1205 may be disposed within the receptacle 524 between the first aperture 527 and the second aperture 531. In general, the keeper 1205 is configured to be releasably coupled to the latch 1020. For example, the keeper 1205 may comprise a base 1305 protruding from the wall 525, and a ledge 1310 extending from the base 1305 toward the second aperture 531 to engage the bar 1110 of the latch 1020 of FIG. 11. In some embodiments, a bump 1315 may also be disposed within the receptacle 524. For example, as illustrated in the embodiment of FIG. 13, the bump 1315 may be disposed between the first aperture 527 and the ledge 1310. In some embodiments, the bump 1315 may be coupled to or otherwise protrude from the base 1305, and preferably has a curved profile. A centralizer pocket 1320 may also be disposed within the receptacle. As illustrated in FIG. 13, the centralizer pocket 1320 may be disposed between the bump 1315 and the first aperture 527, and may be defined at least in part by the bump 1315 and the wall 525 in some embodiments.

Figure 14A:
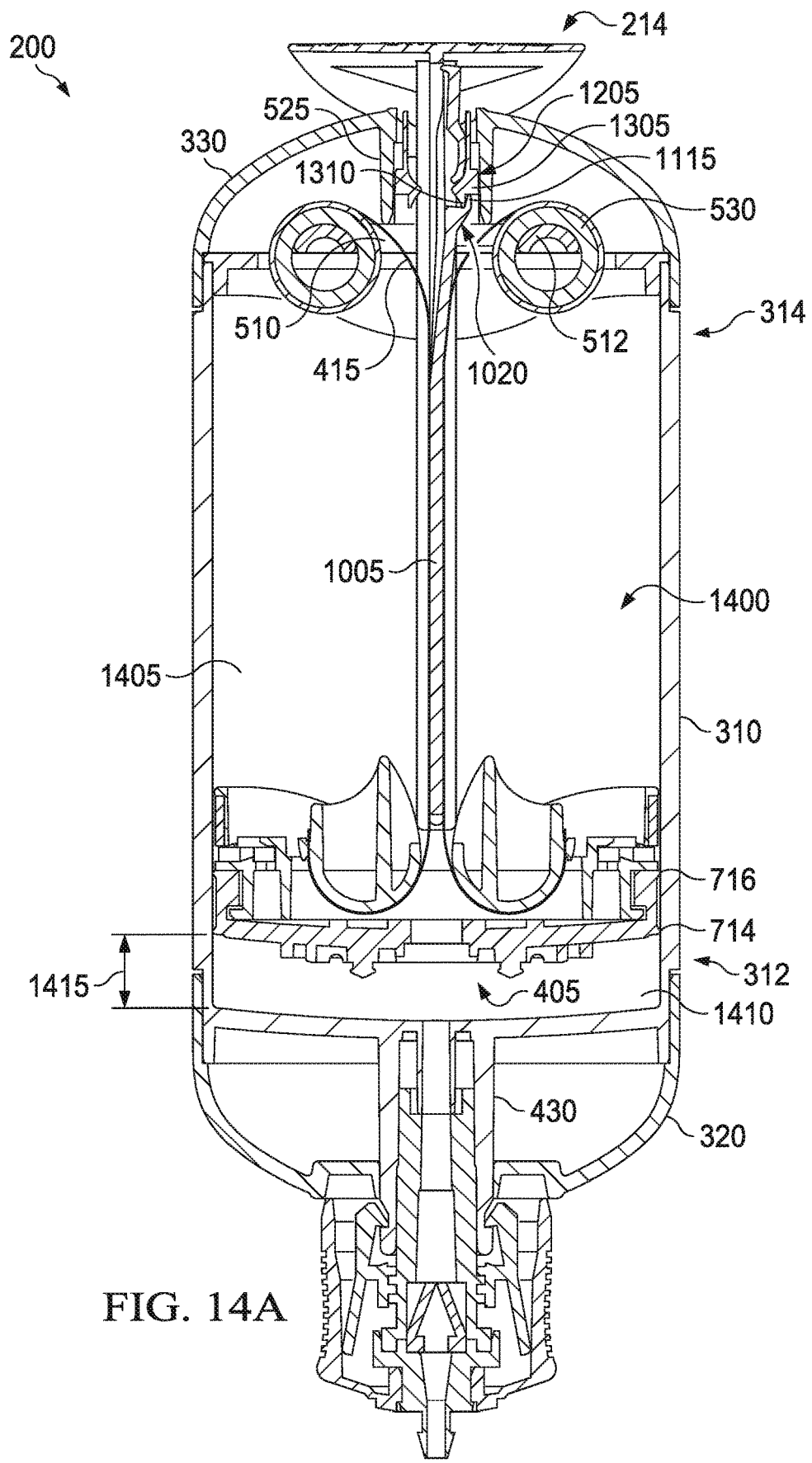
FIG. 14A is a section view of the therapy unit of FIG. 3B.

FIG. 14A is a section view of the therapy unit 200 of FIG. 3B taken along line 14A-14A, illustrating additional details that may be associated with some embodiments of the piston assembly 405 in a charged position, and the actuator 214 in a locked position. In general, assembled as shown in FIG. 14A, the piston assembly 405 and the spring assembly 410 are disposed within the housing 310. In the charged position, the piston assembly 405 is near the distal end 312 of the housing 310 as illustrated in the example of FIG. 14A. The spring assembly 410 may be coupled to the proximal end 314 of the housing 310, and the piston assembly 405 may be disposed between the distal end 312 and the spring assembly 410. The distal cap 320 can be coupled to the distal end 312 of the housing 310 over the conduit 430, and the proximal cap 330 can be coupled to the proximal end 314 of the housing 310 over the spring assembly 410 to define a working chamber 1400 within the therapy unit 200.

The piston assembly 405 generally divides the working chamber 1400 into a proximal chamber 1405 and a distal chamber 1410. The piston assembly 405 can reciprocate in the working chamber 1400 between the distal end 312 and the proximal end 314 of the housing 310, changing the volume of the proximal chamber 1405 and the distal chamber 1410 as it moves. For example, the piston assembly 405 can move along a longitudinal axis of the working chamber toward the proximal end 314 to increase the volume of the distal chamber 1410. The maximum and minimum volume of the distal chamber 1410 may vary, but a volume of less than 1000 cc may be suitable for many applications. A volume of 150 cc or less may be preferable for some applications. The piston assembly 405 preferably provides a seal between the proximal chamber 1405 and the distal chamber 1410. For example, the ridges 714 and 716 may be configured to be in a sliding contact with the interior surface of the housing 310, providing a sealed contact while limiting sliding friction.

The springs 415 may couple the piston assembly 405 to the spring assembly 410. For example, each of the springs 415 may have a proximal end coupled to one of the bushings 530, which may be mounted on the rails 512 of the spring retainer 510. Each of the springs 415 may further have a first portion rolled around a respective bushing 530, a second portion extending through the central opening 740 of the piston 720, and a distal end coupled to the spring retaining structures 942. In the example embodiment of FIG. 14A, the retaining structures 942 may be configured to be inserted into apertures provided on the springs 415, and may or may not maintain their coupling using residual spring force that may be present in the springs 415 in the retracted configuration. However, the retaining structures 942 and the springs 415 may have any of a variety of other coupling configurations. For example, in some embodiments the retaining structures 942 may comprise posts that block displacement of T-shaped spring ends. Curved support surfaces 944 between the central opening 740 and the retaining structures 942 may be configured to push against the springs 415. In some examples, the length of the curved support surfaces 944 between the central opening 740 and the retaining structures 942 may be at least one or one and a half times the width of the springs 415, while in other examples may be two or three times or four times the width of the springs 415. In some examples, the curved support surfaces 944 may provide a substantial surface area to distribute the pushing forces and may reduce the risk of damage to the springs 415. The convex supports 746 may also support the springs 415 as the springs 415 converge into the central opening 740. The convex supports 746 may have a curved length of at least about the width of the springs 415, but in other examples may be at least two or three times the width of the springs 415. The concave region 748 may accommodate the springs 415 and the spring carriers 520 when the piston assembly 405 is in a retracted configuration.

Although the example embodiments of the piston assembly 405 and the spring assembly 410 are illustrated with only two springs, other configurations may be suitable for some applications. The number of springs, the type of springs, and the width and length of the springs may be varied, and in other examples, elastic elements such as sealed pneumatic shocks may be used.

FIG. 14A illustrates the piston assembly 405 near the distal end 312 with the springs 415 elongated and in tension, with a gap 1415 between the distal end 312 and the piston assembly 405. While in this position, the latch 1020 may be coupled to the keeper 1205 to prevent movement of the piston assembly 405 toward the proximal end 314. For example, in the embodiment illustrated in FIG. 14A, the point 1115 may be disposed between the wall 525 and the ledge 1310. The base 1305 can resist the force of the springs 415 applied to the point 1115 through the piston assembly 405 and the shaft 1005 to prevent movement of the piston assembly 405 toward the proximal end 314. In the example embodiment of FIG. 14A, the spring 1025 may be configured to bias the latch 1020 toward the shaft 1005. The ledge 1310 can resist the force of the spring 1025 applied to the latch 1020 to prevent the point 1115 from disengaging the base 1305.

Figure 14B:
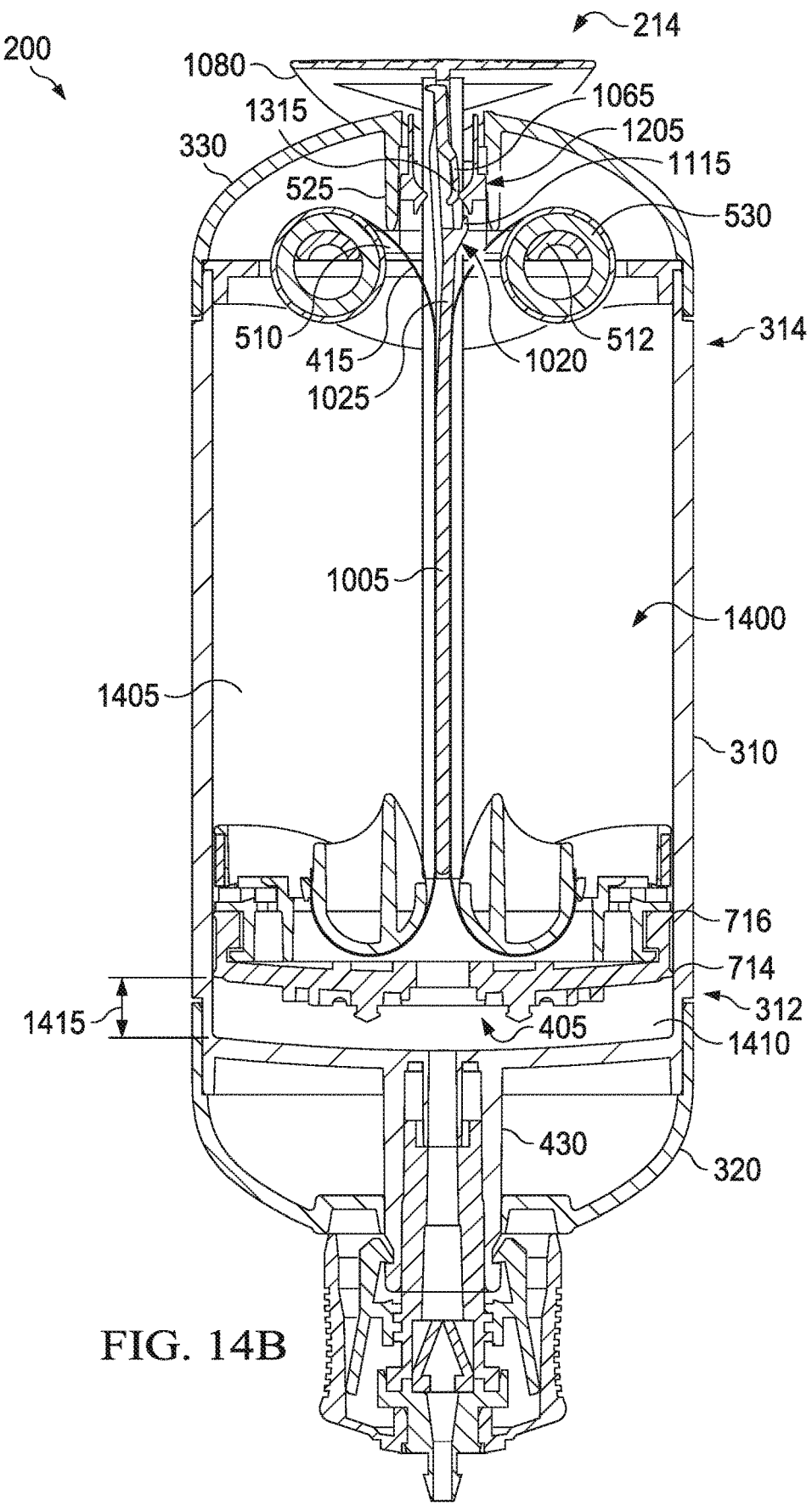
FIG. 14B is a second section view of the therapy unit of FIG. 3B.

FIG. 14B is a section view of the therapy unit 200 of FIG. 3B taken along line 14A-14A, illustrating additional details that may be associated with an example of releasing the actuator 214 and activating the therapy unit 200. From the position illustrated in FIG. 14A, a force may be applied to the handle 1080 to move the piston assembly 405 toward the distal end 312. Although the size of the gap 1415 may vary, the gap 1415 is at least sufficiently large to allow the actuator 214 to move the piston assembly 405 far enough toward the distal end 312 to release the latch 1020 from the keeper 1205. For example, the gap 1415 may be slightly larger than the depth of the throat 1120 to allow the point 1115 to slide past the ledge 1310. In the example embodiment of FIG. 14B, the spring 1025 can bias the latch 1020 toward a centerline or neutral axis of the shaft 1005. If the latch 1020 is released from the keeper 1205, the force of the spring 1025 can move the latch 1020 toward the shaft 1005 past the keeper 1205. Additionally or alternatively, in some embodiments, the centralizer 1065 may also push against the bump 1315 to move the latch 1020 past the keeper 1205 as illustrated in the example of FIG. 14B.

Figure 14C:
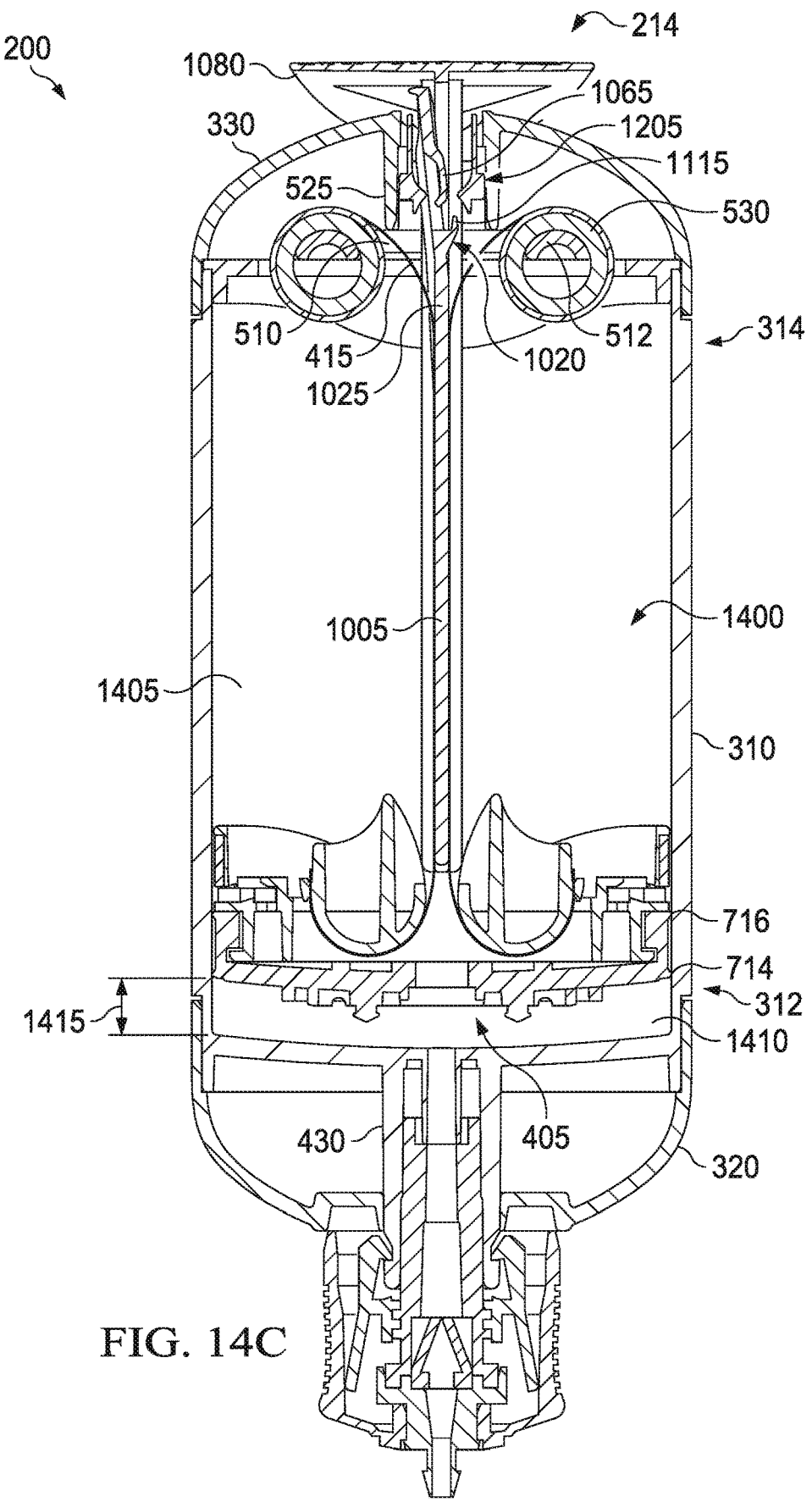
FIG. 14C is a third section view of the therapy unit of FIG. 3B.

FIG. 14C is a section view of the therapy unit 200 of FIG. 3B taken along line 14A-14A, illustrating additional details that may be associated with some embodiments of the actuator 214 in a release position. For example, FIG. 14C may be illustrative of the therapy unit 200 after the latch 1020 is released from the keeper 1205 as illustrated in FIG. 14B, and the spring 1025 returns to its neutral position. In the release position illustrated in the example embodiment of FIG. 14C, the shaft 1005 can move freely through the receptacle 524. For example, the spring 1025 may align the latch 1020 between the keeper 1205 and the opposing wall 525 of the receptacle 524, or as in the embodiment of FIG. 14C, between two keepers 1205.

From the release position of FIG. 14C, the actuator 214 may be returned to the lock position of FIG. 14A, or any force applied to the handle 1080 may be released to activate the therapy unit 200. To return the actuator 214 to the lock position, a first force may be applied through the handle 1080 to overcome the force of the springs 415 and move the latch 1020 toward the distal end 312 past the keeper 1205, and a second force may be applied to the lever 1060 to overcome the opposing force of the spring 1025, pushing the latch 1020 away from the shaft 1005 until it contacts the wall 525 of the receptacle 524. In some embodiments, as illustrated in the example of FIG. 14A, the force applied to the lever 1060 may also overcoming the resistance of the centralizer 1065 bending against the bump 1315. The first force may be released, allowing the force of the springs 415 to move the latch 1020 toward the keeper 1205 until the latch 1020 engages the keeper 1205, substantially as illustrated in FIG. 14A.

In the release position, the actuator 214 may optionally be removed from the housing 310, and the seal 480 may be inserted into the keyway 432. The seal 480 may be any type of seal that may prevent entry of undesired contaminants or other environmental agents (such as water) into the working chamber 1400. In some embodiments, the seal 480 may be tethered to the proximal cap. In still other examples, the seal 480 may be configured with a passageway or slit, and may comprise a deformable material that permits insertion and/or removal of the actuator 214 and reseals upon removal of the actuator 214.

In operation, the dressing 202 may be placed within, over, on, or otherwise proximate to a tissue site, creating a substantially sealed treatment space between the dressing 202 and the tissue site. The dressing 202 may be fluidly coupled to the distal chamber 1410, creating a substantially closed system comprising the distal chamber 1410 and the treatment space. For example, the tube 204 may couple the dressing 202 to the fitting 342.

The springs 415 bias the piston assembly 405 toward the proximal end 314 of the therapy unit 200. In the example embodiment of FIG. 14A, the springs 415 bias the piston assembly 405 toward the spring assembly 410, which is coupled to the proximal end 314. The therapy unit 200 may be primed by moving the piston assembly 405 toward the distal end 312. For example, the distal end 1085 of the actuator 214 may be inserted through the keyway 432 of the proximal cap 330 and the receptacle 524 to engage the piston 720. Force may be applied against the handle 1080 to push the distal end 1085 against the piston 720. As illustrated in FIG. 14A, some embodiments of the distal end 1085 may not be configured to couple or attach to the piston 720, but in other embodiments the distal end 1085 and the piston 720 may be configured to form a complementary interlocking fit or interference fit. The guide channels 1210 can provide additional stability and facilitate tracking of the actuator 214 in the working chamber 1400. If sufficient force is applied to the handle 1080 to overcome the opposing force of the springs 415, the piston assembly 405 can be separated from the spring assembly 410 and moved toward the distal end 312.

From a charged position, such as illustrated in the example embodiment of FIG. 14A, the actuator 214 may be pushed into the housing 310 to release the latch 1020 from the keeper 1205 and activate the therapy unit 200. The springs 415 can move the piston assembly 405 toward the proximal end 314, increasing the volume of the distal chamber 1410 until the elastic force of the springs 415 and the pressure differential across the piston assembly 405 reach a state of equilibrium. Increasing the volume of the distal chamber 1410 can also increase the volume of the closed system, which can decrease the fluid pressure in the closed system substantially according to Boyle's Law.

The reduction in pressure can also draw exudate from the tissue site into the distal chamber 1410. In some embodiments, the distal chamber 1410 can be used to collect exudate, similar or analogous to the container 112.

Leaks or other conditions can increase the pressure in the closed system, disturbing the state of equilibrium between elastic force of the springs 415 and the pressure differential across the piston assembly 405. The elastic force of the springs 415 can move the piston assembly 405 further toward the proximal end 314, increasing the volume of the distal chamber 1410 and decreasing the pressure until a new equilibrium condition is reached, or until the piston assembly 405 is stopped by the spring assembly 410 or other limit structure. In some embodiments, the springs 415 can be selected or calibrated to provide a prescribed pressure in the closed system, and can maintain a substantially constant pressure across the range of motion of the piston assembly 405 in the working chamber 1400.

The therapy unit 200 may be discharged, for example, if movement of the piston assembly 405 toward the proximal end 314 is constrained and the pressure in the closed system exceeds the prescribed pressure. In some embodiments, the therapy unit 200 may be charged again when it is discharged, or from any interim state. For example, the actuator 214 may be used to return the piston assembly 405 to the distal end 312. The actuator 214 may be returned to the locked position of FIG. 14A to hold the piston assembly 405 in the charged position, or the actuator 214 may be released to activate or continue negative-pressure therapy.

The systems, apparatuses, and methods described herein may provide significant advantages. For example, an actuator such as the actuator 214 can be released with a push-down motion, and can be released with a single hand if held against a firm surface. An actuator such as the actuator 214 also eliminates or substantially reduces risk of inadvertently locking a negative-pressure source while recharging. An actuator with a low profile handle, such as the example embodiment of the actuator 214 of FIG. 10, can also significantly reduce packaging requirements. A centralizer, such as the centralizer 1065, can facilitate release and extend the useful life of an actuator.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the actuator 214, the spring carrier 520, or both may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for priming a piston in a housing, the apparatus comprising:
   a shaft comprising a proximal end and a distal end, the distal end for insertion through an opening in the housing to engage the piston, the proximal end being coupled to a handle opposite the distal end;
   a latch for releasably coupling to a keeper disposed in the housing, the latch comprising a base and a bar extending toward the proximal end of the shaft; and
   a spring biasing the latch toward the shaft, wherein the latch is coupled to the shaft by the spring, wherein a first end of the spring is coupled to the shaft opposite the proximal end of the shaft, and wherein the latch is proximate to a second end of the spring that extends free opposite the distal end of the shaft and toward the handle.

2. The apparatus of claim 1, wherein the spring is a flat spring disposed within an aperture of the shaft.

3. The apparatus of claim 1, wherein the spring is a cantilever spring.

4. The apparatus of claim 1, wherein:
the shaft is a beam; and
the spring is a flat spring disposed within a plane of the shaft.

5. The apparatus of claim 1, wherein:
the shaft is a beam; and
the spring is a cantilever spring.

6. The apparatus of claim 1, wherein the spring is a flat spring, and further comprising a centralizer configured to bias the flat spring toward the shaft.

7. The apparatus of claim 6, wherein the centralizer is a cantilevered beam having a free end opposite the proximal end of the shaft.

8. The apparatus of claim 6, wherein the centralizer comprises a bow.

9. The apparatus of claim 1, wherein:
the shaft comprises an aperture; and
the spring is a cantilever spring coupled to the shaft and disposed within the aperture such that the spring and the shaft have collinear neutral axes and the spring lies in a plane defined by edges of the shaft.

10. The apparatus of claim 1, further comprising a lever coupled to the spring.

11. The apparatus of claim 10, wherein the latch comprises a hook.

12. The apparatus of claim 1, wherein:
the shaft is a beam having an aperture;
the spring is disposed within the aperture; and
the spring is a cantilever spring.

13. The apparatus of claim 1, wherein:
the shaft is a beam having an aperture;
the spring is disposed within the aperture;
the spring is a cantilever spring; and
a centralizer is coupled to the spring between the latch and the free end to bias the latch toward the shaft.

* * * * *